(12) United States Patent
Stabe et al.

(10) Patent No.: US 6,839,402 B2
(45) Date of Patent: Jan. 4, 2005

(54) METHOD AND APPARATUS FOR EXAMINING ABSORBENT ARTICLES

(75) Inventors: Lisa M. P. Stabe, Kaukauna, WI (US); Timothy L. Schmitz, Menasha, WI (US); Martin J. Garofalo, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 68 days.

(21) Appl. No.: 10/209,961

(22) Filed: Aug. 1, 2002

(65) Prior Publication Data

US 2003/0147490 A1 Aug. 7, 2003

Related U.S. Application Data

(60) Provisional application No. 60/354,753, filed on Feb. 5, 2002.

(51) Int. Cl.[7] .................................................. H05G 1/60
(52) U.S. Cl. .............................. 378/20; 378/4; 378/901; 378/208
(58) Field of Search .............................. 378/20, 4, 901, 378/65, 209, 52, 50, 54; 604/358; 382/100

(56) References Cited

U.S. PATENT DOCUMENTS

| | | | |
|---|---|---|---|
| 4,465,069 A | * | 8/1984 | Barbier et al. .............. 606/130 |
| 4,562,540 A | | 12/1985 | Devaney |
| 4,884,455 A | | 12/1989 | Vinegar et al. |
| 4,982,086 A | | 1/1991 | Withjack |
| 5,063,509 A | | 11/1991 | Coles et al. |
| 5,164,590 A | | 11/1992 | Coles et al. |
| 5,331,155 A | * | 7/1994 | Blauch ....................... 250/255 |
| 5,537,454 A | * | 7/1996 | Korver, II ..................... 378/65 |
| 5,568,384 A | | 10/1996 | Robb et al. |
| 5,625,661 A | | 4/1997 | Oikawa |
| 5,696,806 A | | 12/1997 | Grodzins et al. |
| 6,026,171 A | * | 2/2000 | Hiraoglu et al. ............. 382/100 |
| 6,103,952 A | * | 8/2000 | Coles et al. ................. 604/358 |

FOREIGN PATENT DOCUMENTS

| | | |
|---|---|---|
| EP | 0 269 280 B1 | 3/1993 |
| EP | 0 489 151 B1 | 5/1997 |
| EP | 0 875 751 a1 | 11/1998 |
| WO | WO 00/46592 A2 | 8/2000 |

OTHER PUBLICATIONS

Written Opinion for PCT/US 03/00880, dated Apr. 2, 2004, 6 pages.

* cited by examiner

Primary Examiner—Craig E. Church
Assistant Examiner—Irakli Kiknadze
(74) Attorney, Agent, or Firm—Senninger Rogers

(57) ABSTRACT

A radiological system for analyzing an absorbent article including a radiological device for collecting radiological data from the absorbent article, a support mountable adjacent the radiological device for holding the absorbent article, and a computing device operatively connected to the radiological device having a program for analyzing the data collected by the radiological device.

36 Claims, 19 Drawing Sheets

FIG. 11
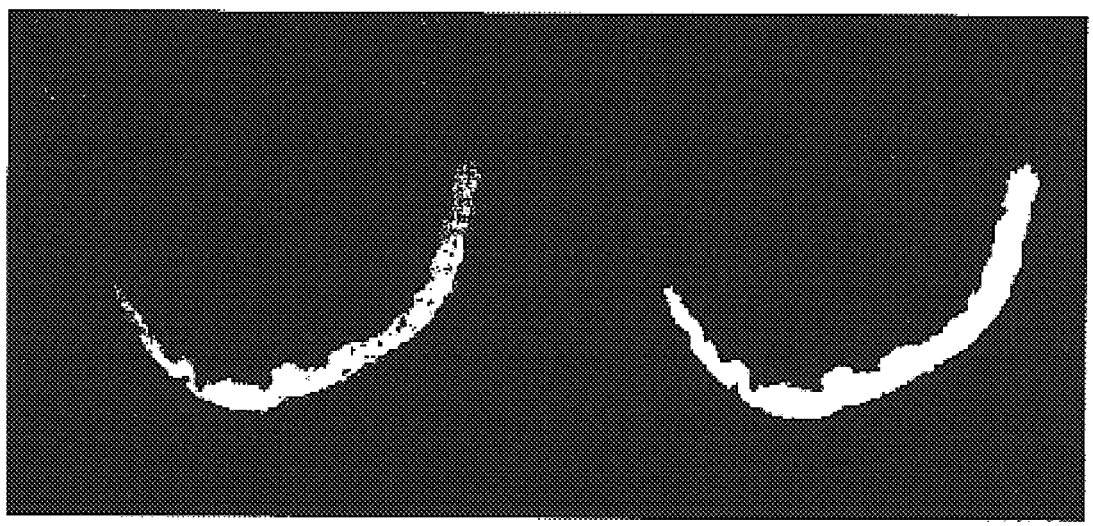
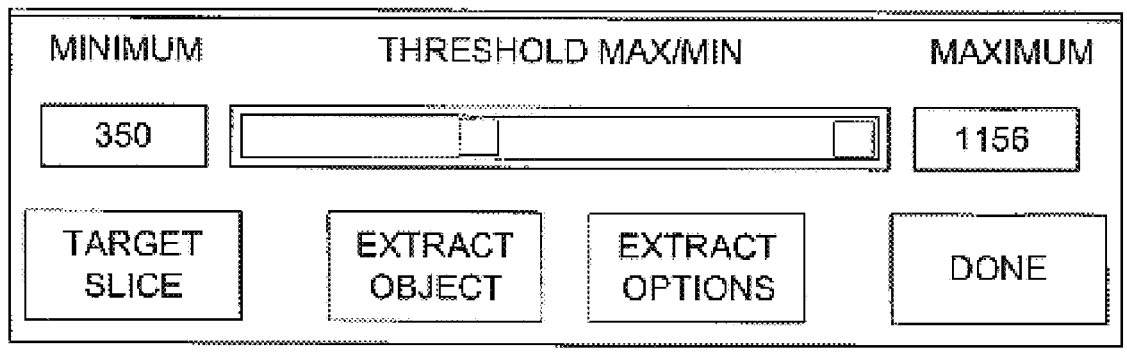

FIG. 15

| Sample Options - Region Of Interest | ROI.Stats-- Re... |
|---|---|
| Sample Type ☐ 1.Object<br>○ Selected Region<br>⊙ Object[s]<br>○ Individual Voxels<br>Select All / Invert Selections<br>Combine Objects ⊙ No ○ Yes<br>Minimum Sample Max/Min Maximum<br>[560] [_____] [1211]<br>Range ⊙ Volume ○ Data Type<br>Volume ⊙ Primary ○ Related<br>Summing ⊙ On ○ Off [Reset Sum]<br>Auto Reset ⊙ On ○ Off<br>Sample ⊙ All Slices ○ Slices Specified in Slice Menu<br>Sequences Display ○ On ⊙ Off<br>Stat Type ⊙ Intensity ○ Shape ○ Fractal<br>○ Boundary Coordinates ○ Region Pixels<br>Decimal Places [2]<br>Stats ○ On ⊙ Off [Configure Log Stats]<br>[DONE] | ☐ Vol. No. = 1<br>☐ Slice = 55<br>☑ Regnn Name = 1 Object_sum<br>☐ Maximum = 1105.<br>☐ at 108,184,127.<br>☐ Minimum = 0.<br>☐ at,1,1,1]<br>☐ Mean = 17.61<br>☐ St. Dev- 06.98<br>☐ Sum = 151474087<br>☐ Number of Voxels = 8602500<br>☐ Area - 0802500, mm2<br>☐ Volume = 8602500 mm3<br>☐ <560 = 8485717<br>☑ >1211 = 0<br>☑ >= 560 &<= 1211 = 116783<br>☐ Mean In Flange = 876.06<br>☐ Standard Deviation In Range = 1<br>☐ Sum In Range = 02309381.<br>☐ BAP = 369 0901.<br>[LOG STATS] [DONE] |

FIG. 16

VOLUME=DIAPER
SAMPLE MAX = 1211
SAMPLE MIN = 560

| SLICE | NAME | S MAX | BETWEEN |
|---|---|---|---|
| 1 | 1. OBJECT | 0 | 0 |
| 2 | 1. OBJECT | 0 | 0 |
| 3 | 1. OBJECT | 0 | 0 |
| 4 | 1. OBJECT | 0 | 0 |
| 5 | 1. OBJECT | 0 | 0 |
| 6 | 1. OBJECT | 0 | 0 |
| 7 | 1. OBJECT | 0 | 0 |
| 8 | 1. OBJECT | 0 | 0 |
| 9 | 1. OBJECT | 0 | 0 |
| 10 | 1. OBJECT | 0 | 0 |
| 11 | 1. OBJECT | 0 | 0 |
| 12 | 1. OBJECT | 0 | 0 |
| 13 | 1. OBJECT | 0 | 2 |
| 14 | 1. OBJECT | 0 | 1 |
| 15 | 1. OBJECT | 0 | 0 |
| 16 | 1. OBJECT | 0 | 13 |
| 17 | 1. OBJECT | 0 | 33 |
| 18 | 1. OBJECT | 0 | 47 |
| 19 | 1. OBJECT | 0 | 46 |
| 20 | 1. OBJECT | 0 | 37 |
| 21 | 1. OBJECT | 0 | 50 |
| 22 | 1. OBJECT | 0 | 73 |
| 23 | 1. OBJECT | 0 | 93 |
| 24 | 1. OBJECT | 0 | 95 |
| 25 | 1. OBJECT | 0 | 98 |
| 26 | 1. OBJECT | 0 | 99 |
| 27 | 1. OBJECT | 0 | 113 |
| 28 | 1. OBJECT | 0 | 124 |
| 29 | 1. OBJECT | 0 | 114 |
| 30 | 1. OBJECT | 0 | 100 |
| 31 | 1. OBJECT | 0 | 96 |
| 32 | 1. OBJECT | 0 | 106 |
| 33 | 1. OBJECT | 0 | 124 |
| 34 | 1. OBJECT | 0 | 117 |
| 35 | 1. OBJECT | 0 | 120 |
| 36 | 1. OBJECT | 0 | 158 |

CONTINUES TO PG. 17

CONTINUES FROM PG. 16

| | | | |
|---|---|---|---|
| 37 | 1. OBJECT | 0 | 241 |
| 38 | 1. OBJECT | 0 | 333 |
| 39 | 1. OBJECT | 0 | 340 |
| 40 | 1. OBJECT | 0 | 379 |
| 41 | 1. OBJECT | 0 | 446 |
| 42 | 1. OBJECT | 0 | 574 |
| 43 | 1. OBJECT | 0 | 675 |
| 44 | 1. OBJECT | 0 | 666 |
| 45 | 1. OBJECT | 0 | 682 |
| 46 | 1. OBJECT | 0 | 754 |
| 47 | 1. OBJECT | 0 | 843 |
| 48 | 1. OBJECT | 0 | 933 |
| 49 | 1. OBJECT | 0 | 949 |
| 50 | 1. OBJECT | 0 | 994 |
| 51 | 1. OBJECT | 0 | 1058 |
| 52 | 1. OBJECT | 0 | 1113 |
| 53 | 1. OBJECT | 0 | 1145 |
| 54 | 1. OBJECT | 0 | 1227 |
| 55 | 1. OBJECT | 0 | 1308 |
| 56 | 1. OBJECT | 0 | 1449 |
| 57 | 1. OBJECT | 0 | 1545 |
| 58 | 1. OBJECT | 0 | 1598 |
| 59 | 1. OBJECT | 0 | 1634 |
| 60 | 1. OBJECT | 0 | 1684 |
| 61 | 1. OBJECT | 0 | 1758 |
| 62 | 1. OBJECT | 0 | 1809 |
| 63 | 1. OBJECT | 0 | 1844 |
| 64 | 1. OBJECT | 0 | 1846 |
| 65 | 1. OBJECT | 0 | 1854 |
| 66 | 1. OBJECT | 0 | 1860 |
| 67 | 1. OBJECT | 0 | 1861 |
| 68 | 1. OBJECT | 0 | 1873 |
| 69 | 1. OBJECT | 0 | 1875 |
| 70 | 1. OBJECT | 0 | 1878 |
| 71 | 1. OBJECT | 0 | 1880 |
| 72 | 1. OBJECT | 0 | 1889 |
| 73 | 1. OBJECT | 0 | 1882 |
| 74 | 1. OBJECT | 0 | 1887 |
| 75 | 1. OBJECT | 0 | 1886 |
| 76 | 1. OBJECT | 0 | 1885 |
| 77 | 1. OBJECT | 0 | 1888 |
| 78 | 1. OBJECT | 0 | 1889 |
| 79 | 1. OBJECT | 0 | 1909 |
| 80 | 1. OBJECT | 0 | 1924 |
| 81 | 1. OBJECT | 0 | 1935 |
| 82 | 1. OBJECT | 0 | 1947 |
| 83 | 1. OBJECT | 0 | 1966 |

CONTINUES TO PG. 18

CONTINUES FROM PG. 17

| | | | |
|---|---|---|---|
| 84 | 1. OBJECT | 0 | 1953 |
| 85 | 1. OBJECT | 0 | 1953 |
| 86 | 1. OBJECT | 0 | 1953 |
| 87 | 1. OBJECT | 0 | 1962 |
| 88 | 1. OBJECT | 0 | 1950 |
| 89 | 1. OBJECT | 0 | 1931 |
| 90 | 1. OBJECT | 0 | 1916 |
| 91 | 1. OBJECT | 0 | 1891 |
| 92 | 1. OBJECT | 0 | 1889 |
| 93 | 1. OBJECT | 0 | 1880 |
| 94 | 1. OBJECT | 0 | 1831 |
| 95 | 1. OBJECT | 0 | 1733 |
| 96 | 1. OBJECT | 0 | 1583 |
| 97 | 1. OBJECT | 0 | 1463 |
| 98 | 1. OBJECT | 0 | 1399 |
| 99 | 1. OBJECT | 0 | 1358 |
| 100 | 1. OBJECT | 0 | 1285 |
| 101 | 1. OBJECT | 0 | 1185 |
| 102 | 1. OBJECT | 0 | 1121 |
| 103 | 1. OBJECT | 0 | 1080 |
| 104 | 1. OBJECT | 0 | 1064 |
| 105 | 1. OBJECT | 0 | 1049 |
| 106 | 1. OBJECT | 0 | 1031 |
| 107 | 1. OBJECT | 0 | 1020 |
| 108 | 1. OBJECT | 0 | 1022 |
| 109 | 1. OBJECT | 0 | 998 |
| 110 | 1. OBJECT | 0 | 955 |
| 111 | 1. OBJECT | 0 | 901 |
| 112 | 1. OBJECT | 0 | 881 |
| 113 | 1. OBJECT | 0 | 893 |
| 114 | 1. OBJECT | 0 | 802 |
| 115 | 1. OBJECT | 0 | 664 |
| 116 | 1. OBJECT | 0 | 541 |
| 117 | 1. OBJECT | 0 | 494 |
| 118 | 1. OBJECT | 0 | 483 |
| 119 | 1. OBJECT | 0 | 389 |
| 120 | 1. OBJECT | 0 | 267 |
| 121 | 1. OBJECT | 0 | 184 |
| 122 | 1. OBJECT | 0 | 177 |
| 123 | 1. OBJECT | 0 | 185 |
| 124 | 1. OBJECT | 0 | 175 |
| 125 | 1. OBJECT | 0 | 164 |
| 126 | 1. OBJECT | 0 | 172 |
| 127 | 1. OBJECT | 0 | 197 |
| 128 | 1. OBJECT | 0 | 208 |
| 129 | 1. OBJECT | 0 | 195 |
| 130 | 1. OBJECT | 0 | 160 |

CONTINUES TO PG. 19

CONTINUES FROM PG. 18

| | | | |
|---|---|---|---|
| 131 | 1. OBJECT | 0 | 130 |
| 132 | 1. OBJECT | 0 | 118 |
| 133 | 1. OBJECT | 0 | 115 |
| 134 | 1. OBJECT | 0 | 81 |
| 135 | 1. OBJECT | 0 | 44 |
| 136 | 1. OBJECT | 0 | 24 |
| 137 | 1. OBJECT | 0 | 16 |
| 138 | 1. OBJECT | 0 | 12 |
| 139 | 1. OBJECT | 0 | 2 |
| 140 | 1. OBJECT | 0 | 0 |
| 141 | 1. OBJECT | 0 | 0 |
| 142 | 1. OBJECT | 0 | 0 |
| 143 | 1. OBJECT | 0 | 0 |
| 144 | 1. OBJECT | 0 | 0 |
| 145 | 1. OBJECT | 0 | 0 |
| 146 | 1. OBJECT | 0 | 0 |
| 147 | 1. OBJECT | 0 | 0 |
| 148 | 1. OBJECT | 0 | 0 |
| 149 | 1. OBJECT | 0 | 0 |
| 150 | 1. OBJECT | 0 | 0 |
| 151 | 1. OBJECT | 0 | 0 |
| 152 | 1. OBJECT | 0 | 0 |
| 153 | 1. OBJECT | 0 | 0 |
| 154 | 1. OBJECT | 0 | 0 |
| 155 | 1. OBJECT | 0 | 0 |
| 155 | 1. OBJECT_SUM | 0 | 116783 |

METHOD AND APPARATUS FOR EXAMINING ABSORBENT ARTICLES

CROSS-REFERENCE TO RELATED APPLICATION

This application claims the benefit of U.S. Provisional Application No. 60/354,753, filed Feb. 5, 2002.

BACKGROUND OF THE INVENTION

The present invention relates generally to radiological systems and procedures, and more particularly to radiological systems and procedures for examining substances in absorbent articles.

Absorbent articles such as panty liners, feminine napkins, tampons, interlabial pads, other feminine care articles, diapers, training pants, other child and infant care articles, incontinence articles, and other adult care articles are used to absorb various body waste such as urine, feces and menses. In order to analyze these articles to determine the effectiveness of the articles and to make improvements to them, it is necessary to accurately examine the amounts and locations of the waste in the articles. In the past, the amounts and locations of the waste was determined by visual examination and weighing. Dyes were sometimes used to aid the visual examination. In some instances, the articles were dissected and/or segmented to assess distribution. However, loss and/or redistribution of waste during the dissection or segmentation process caused inaccurate measurement. Radiographic images (i.e., still 2-dimensional x-ray films) have also been used to determine the locations of the waste. However, because radiographic images are two-dimensional, an accurate determination of the locations of the waste could not be made.

SUMMARY OF THE INVENTION

Briefly, apparatus of this invention is a radiological system for analyzing an absorbent article comprising a radiological device for collecting radiological data from the absorbent article, a support mountable adjacent the radiological device for holding the absorbent article, and a computing device operatively connected to the radiological device having a program for analyzing the data collected by the radiological device.

In another aspect, the invention includes a support for holding an absorbent article comprising a base, a post extending upward from the base, an arm extending horizontally from the post, and a platform mounted on the arm opposite the post for holding the absorbent article. The platform includes a generally radiolucent frame having a central opening and grid of generally radiolucent filaments extending across the opening.

In still another aspect, the invention includes an absorbent article, a support for holding the absorbent article, and a computed tomography scanner mounted adjacent the support for collecting radiological data from the absorbent article held by the support.

In yet another aspect, the present invention includes a method of analyzing an absorbent article comprising collecting radiological data from the absorbent article, and numerically analyzing the collected data.

Other features of the present invention will be in part apparent and in part pointed out hereinafter.

BRIEF DESCRIPTION OF THE DRAWINGS

FIG. 11 is a computer display showing a portion of the article selected for extraction;

FIG. 15 is a computer display after a minimum parameter is identified; and

FIG. 16 is a log of slice data.

Corresponding reference characters indicate corresponding parts throughout the several views of the drawings.

DETAILED DESCRIPTION

Figure 1:
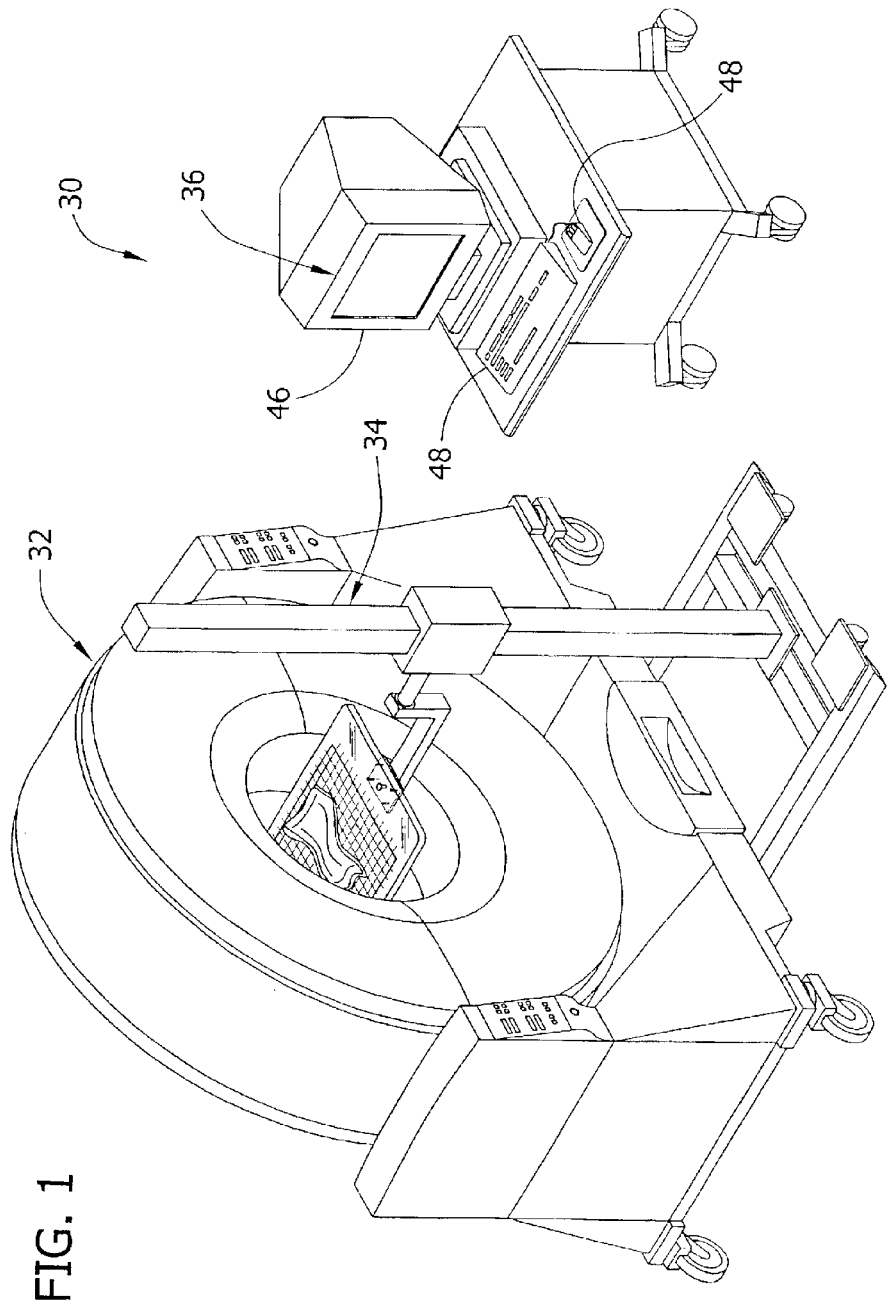
FIG. 1 is a perspective of a radiological system of the present invention.

Referring now to the drawings and in particular to FIG. 1, a radiological system of the present invention is designated in its entirety by the reference numeral 30. Although other radiological systems 30 are contemplated as being within the scope of the present invention, in one embodiment, the system of the present invention generally comprises a radiological device (generally designated by 32) such as an Analogic computed tomography (CT) scanner, an article support (generally designated by 34) and a computer console (generally designated by 36) for controlling operation of the gantry. Analogic is a federally registered trademark of Analogic Corporation of Peabody, Mass. Other radiological devices including radiographic devices (.g., x-ray machines for taking still images) and radioscopic devices (e.g, x-ray machines for taking moving images) are also contemplated as being within the scope of the present invention. Further, systems having other components such as image recognition equipment for extracting data from conventional x-ray images (i.e., those obtained from radiographic devices or radioscopic devices) are also contemplated.

Figure 2:
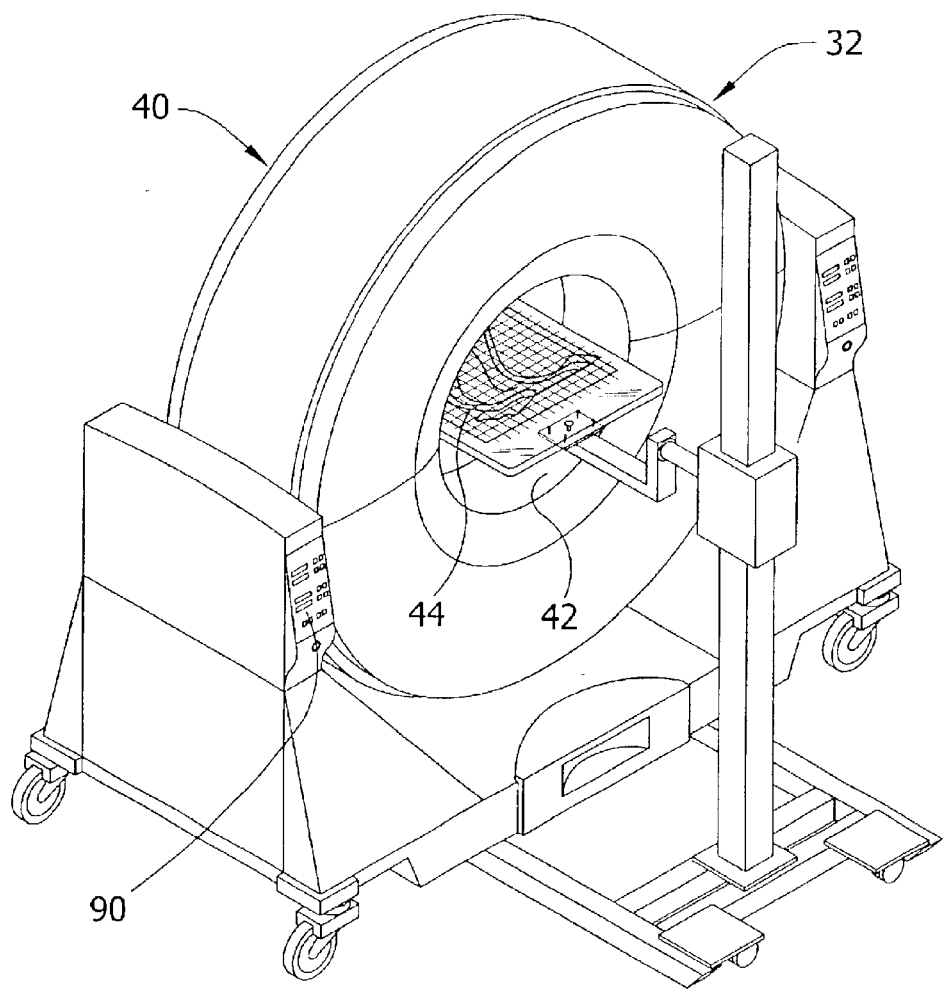
FIG. 2 is a perspective of a radiological device and an article support of the present invention.

As illustrated in FIG. 2, in one embodiment the radiological device 32 is a CT scanner generally comprising a gantry, generally designated by 40, having an opening 42 for receiving an article 44 for analysis. The computer console 36 (FIG. 1) is operatively connected to the radiological device 32 for collecting, reconstructing and preparing data for display on an image display monitor 46. The computer console 36 may include one or more input devices such as a keyboard 48.

Figure 3:
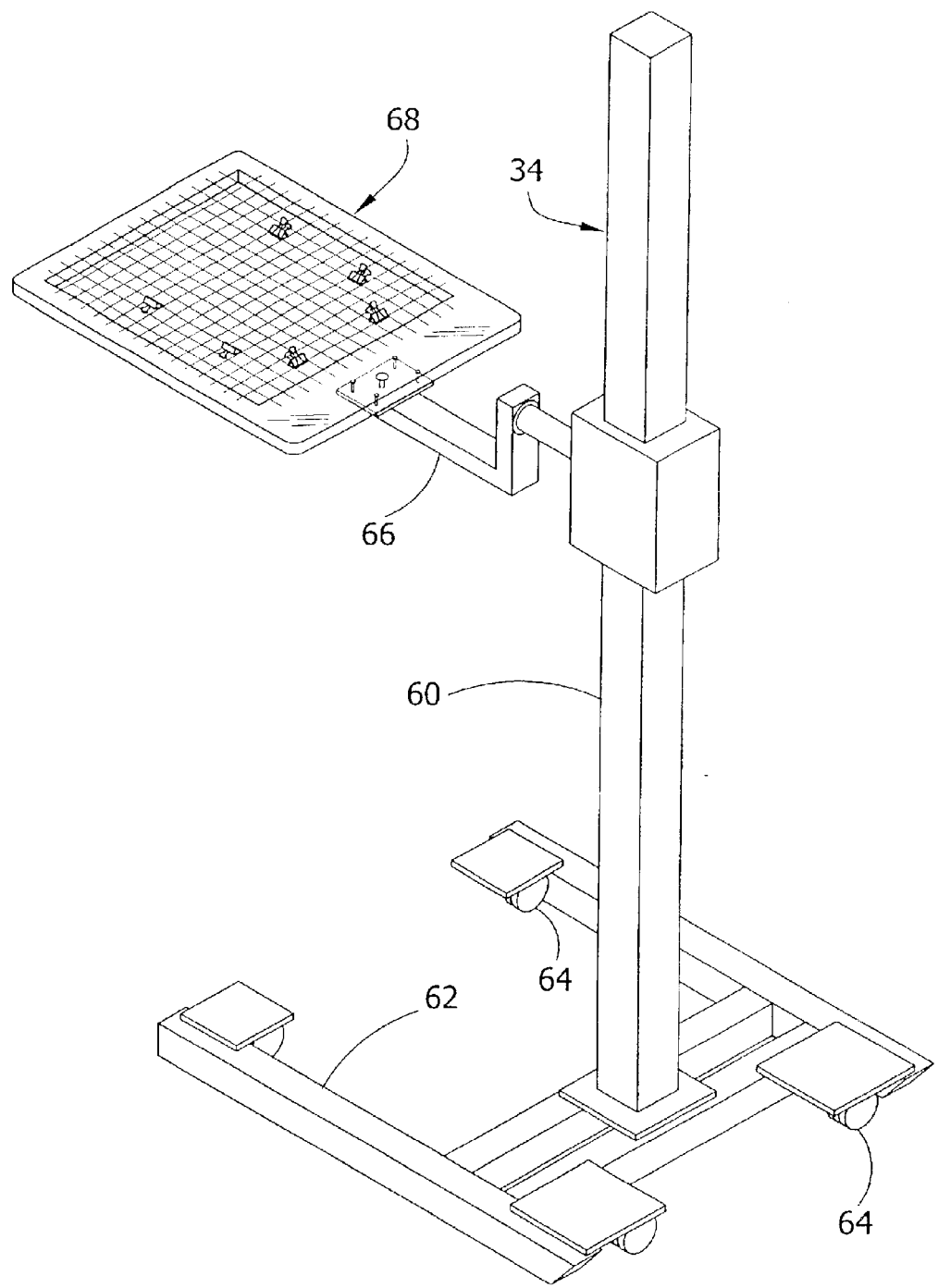
FIG. 3 is a perspective of the article support of the present invention.
Figure 4:
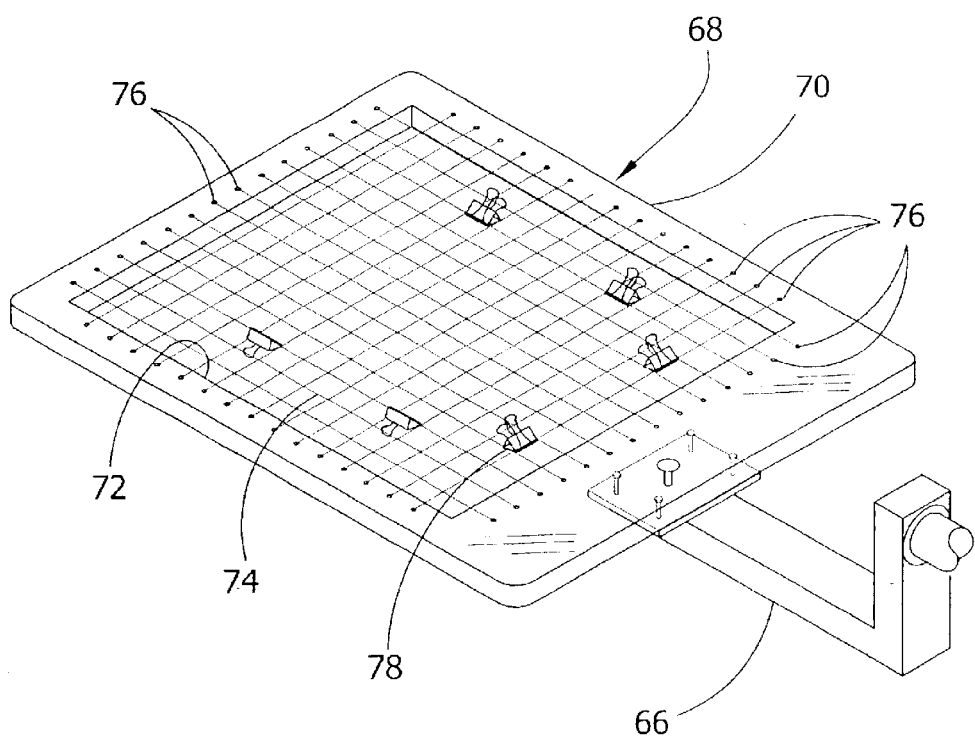
FIG. 4 is a perspective of a platform of the article support of the present invention.
Figure 5:
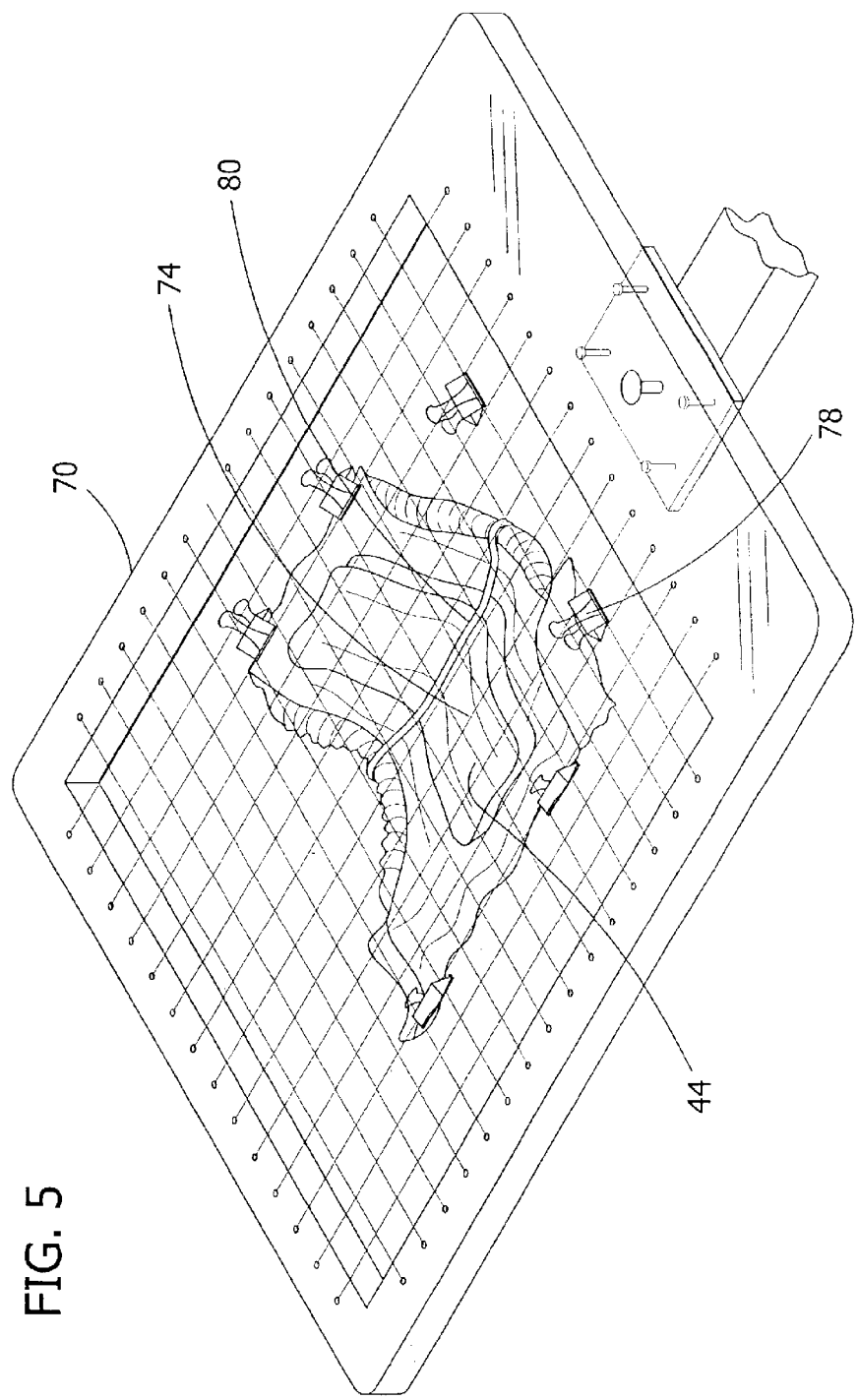
FIG. 5 is a detail of the platform showing an absorbent article suspended therebelow.
Figure 6:
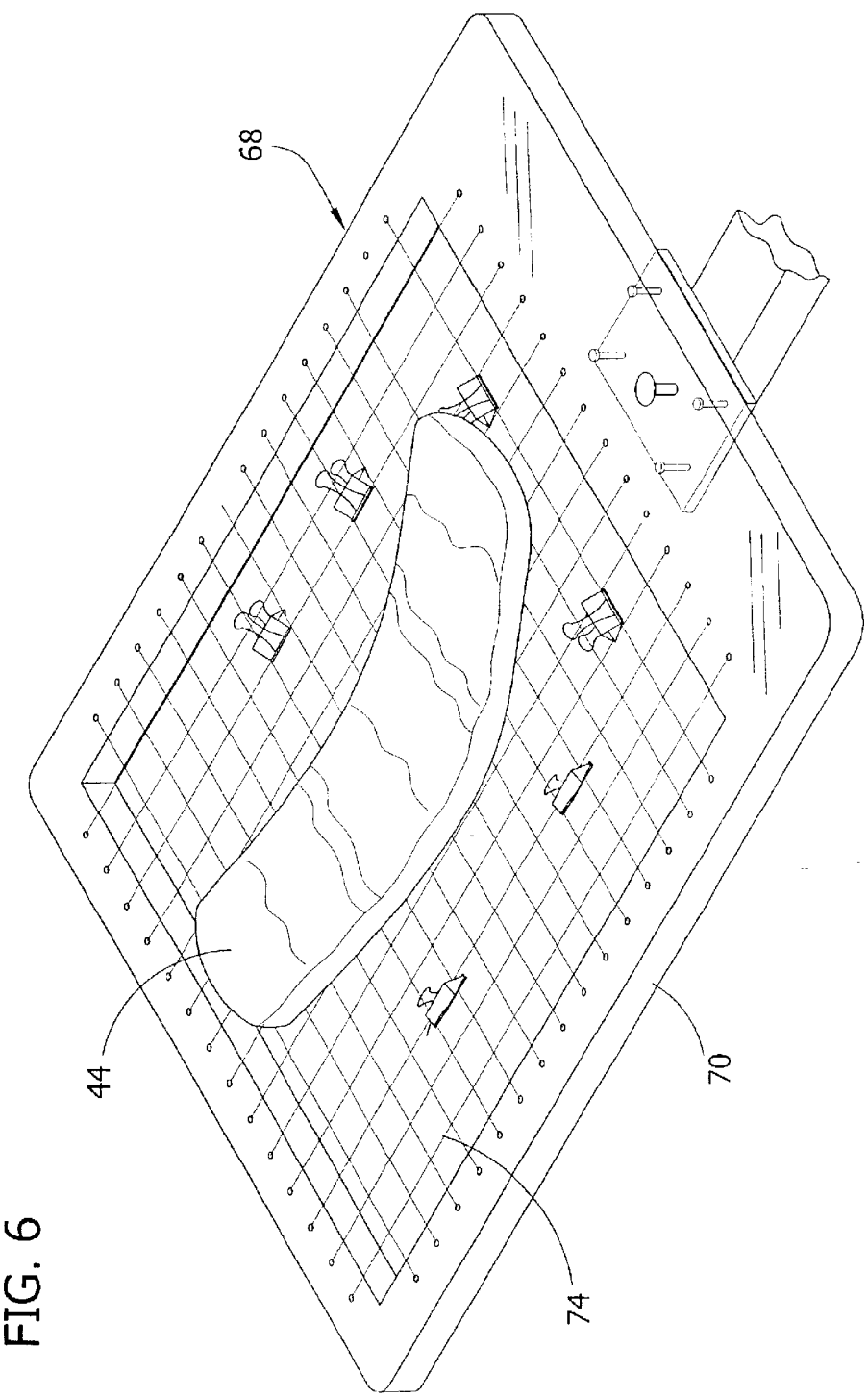
FIG. 6 is a detail of the platform showing an absorbent article positioned thereon.
Figure 7:
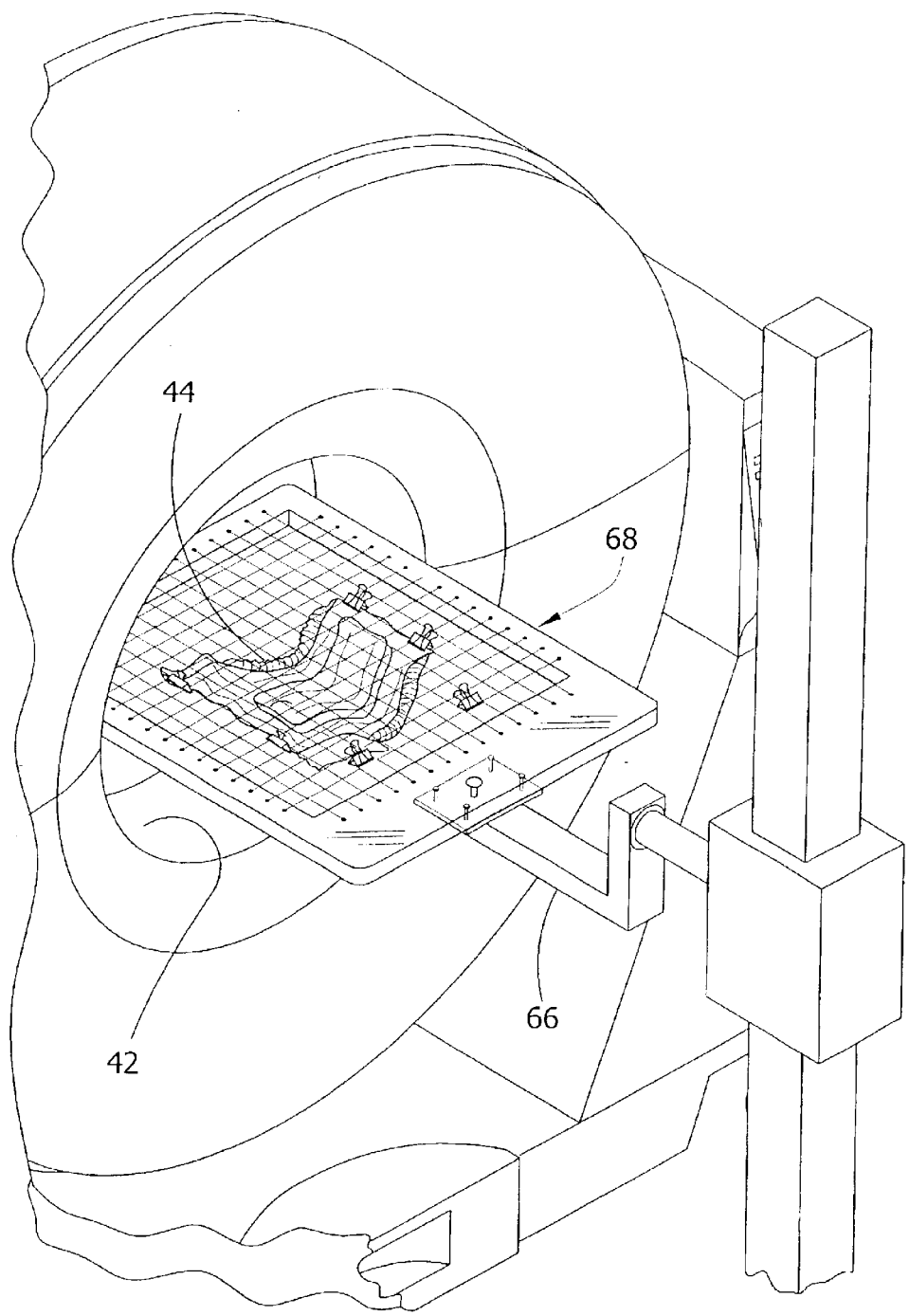
FIG. 7 is a perspective of the platform having the suspended absorbent article positioned in an opening of the radiological device.
Figure 8:
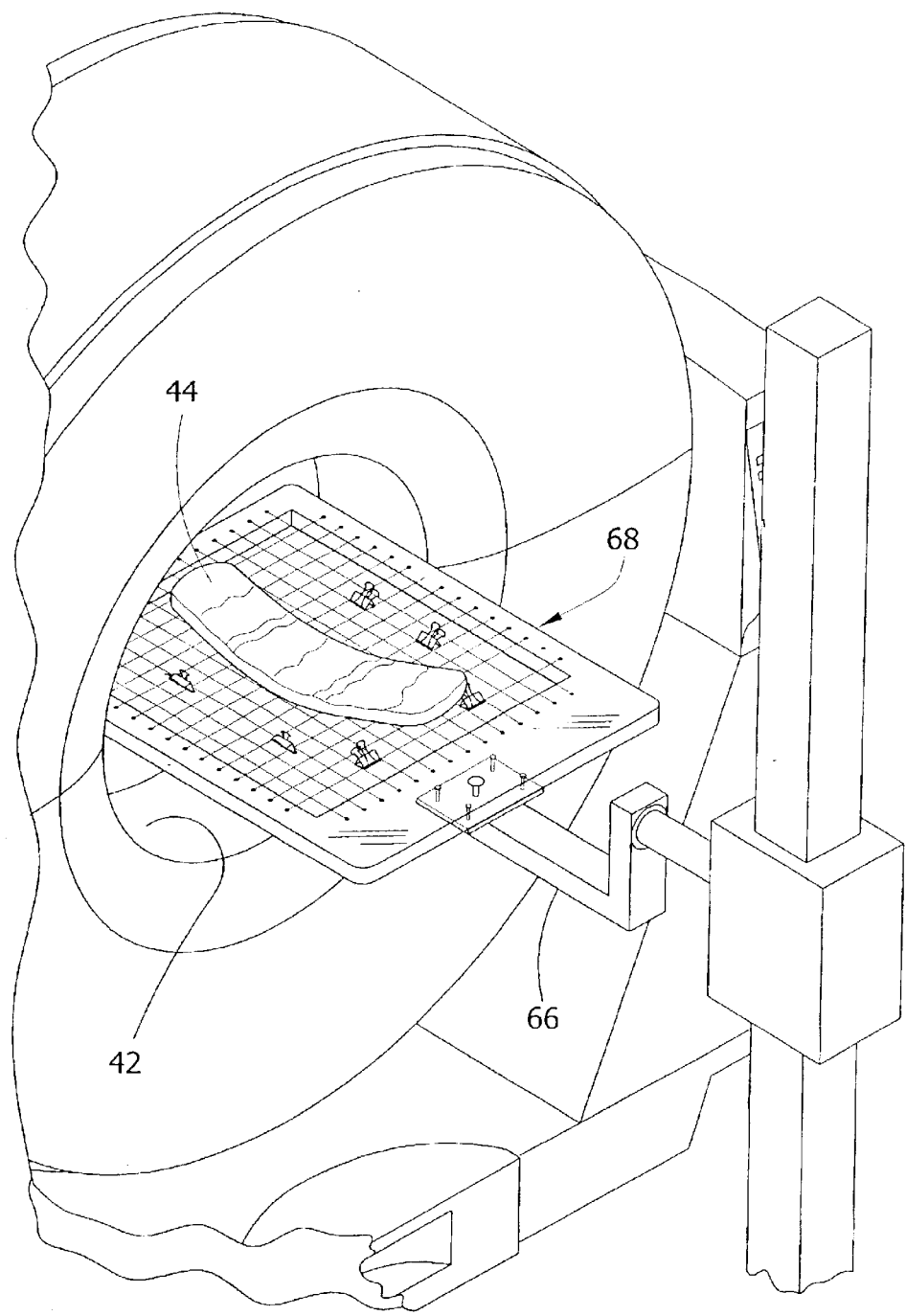
FIG. 8 is a perspective of the platform having the absorbent article thereon positioned in an opening of the radiological device.

As illustrated in FIG. 3, in one embodiment the article support 34 has a vertical post 60 mounted on a base 62 having wheels 64. An arm 66 extends horizontally from the vertical post 60. A platform, generally designated by 68, is mounted at an end of the arm opposite the post 60 for holding the article 44. The arm 66 is movable up and down on the post 60 for adjusting a height of the article 44 (FIG. 2) with respect to the opening 42 in the gantry 40. The wheels 64 on the base 62 of the support 34 permit horizontal positioning of the article 44 relative to the opening 42 in the gantry 40. It is further envisioned that the arm 66 may be pivotable with respect to the post 60 to change the orientation of the article 44 in the gantry 40. As illustrated in FIG. 4, the platform 68 comprises a low density frame 70 having a central opening 72 and grid 74 of low density filaments. In one embodiment, the frame 70 is a rectangular sheet of Lexan material available from General Electric Company of Pittsfield, Mass. (Lexan is a federally registered trademark of General Electric Company.) Holes 76 are formed in the frame 70 around the central opening 72 at intervals (e.g., one inch) for stringing the grid 74. In one embodiment, the grid 74 is formed from monofilament fishing line. Clamps 78 such as conventional binder clips may be mounted on the grid 74 for suspending the article 44 below the frame 70 as illustrated in FIG. 5. Other devices 80 such as conventional rubber bands may be used to maintain the article 44 in a desired shape. Alternatively, the article 44 may be positioned on top of the grid 74 as illustrated in FIG. 6. Since the height of the arm 66 can be changed, the article 44 can be generally centered in the opening 42 in the gantry 40 regardless of whether the article is suspended below the grid 74 as shown in FIG. 7 or positioned on top of the grid 74 as shown in FIG. 8.

The radiographic system 30 also includes one or more computing devices (e.g., a personal computer, not shown) having a program (e.g., AnalyzePC distributed by AnalyzeDirect, Inc. of Lenexa, Kans.) for analyzing the data collected by the radiological device 32.

To prepare the radiological device 32 for operation, the gantry 40 and console 36 are energized. The computer console 36 is booted and the user logs into by entering a username and password. The user then initiates a standard start-up procedure. For the Analogic CT scanner, the computer console 36 offers a "scanner menu". The user selects "warm-up" and then "ok". The user then presses a "start" key on the keyboard 48 when prompted. The user next selects "air tables" under the scanner menu and then "all". The user again presses the "start" key on the keyboard 48 when prompted. After the computer console completes the air tables, the user selects "cancel". Under the "patient menu", the user selects "enter". A warning message concerning warm-up will appear on the monitor 46, and the user selects "cancel". After the start-up, the user may enter information concerning the particular test by entering information in the "patient" menu.

After warm-up, the user selects "to scan". An article 44 is positioned on the support 34 and the gantry 32 is moved to an initial position (e.g., a "350 mm" position) by using controls 90 (FIG. 2) on the gantry. The article 44 is aligned with the gantry 40 using a positioning light (not shown). The article 44 is positioned so the light illuminates a portion of the article where scanning will begin. The user presses a "scanogram" button on the gantry 40 until the gantry stops moving. The scanning protocol is selected by selecting "scanogram" scan type from the menu and then "new". Desired information can be input at the prompt. The user selects "gantry" when prompted for a "move unit" and "in" when prompted for a "direction". The desired scanning parameters are selected by selecting "params" and then "ok"  when done. The desired algorithm is selected. The "patient position" is set to "headfirst/supine". The user selects "head" under the "scanning protocol" menu and then "to scan". After reviewing the set up parameters on the monitor 46, the user enters any desired comments and selects "scan". After the area surrounding the gantry 40 is cleared of bystanders, the "start" button is pressed on the keyboard 48 when prompted. A completed scanogram image will be shown on the monitor 46.

The user proceeds with axial or volume slice scanning by selecting the appropriate item from the menu. When performing volume scanning, an index size is selected for reconstruction. In the "position axial scan" window, the user sets the scanning protocol by selecting "draw" and "plan" for multiple consecutive scans or "draw" and "slice" for a single scan. The user positions the cursor over a desired area on the scanogram and activates the scanning menu. The scanning menu location is adjusted as necessary to a desired position and the scanning parameters are selected. A beam thickness, a slice index, a field of view (FOV), an x-axis and a y-axis are set, and "to scan" is selected from the menu. The user reviews the scanning protocol in the "axial scan status" window for correct set-up, de-selects the "corrected" option, enters any desired comments, and selects "scan". The user presses the "move" button and then the "start" button on keyboard 48 when prompted. Images then appear on the monitor 46. When scanning is complete, the article 44 may be removed from the support 34 or the user can select "set-up" and repeat the scanning.

Once the images are acquired as described above, they may be printed using conventional techniques for the radiological device 32. Further, the images may be archived to disk (e.g., an optical disk) using conventional techniques for the particular device 32. After the images are printed and/or archived, the user may exit from the scanner software.

When all images are obtained, the user accesses the "image" menu and records the time of the first image and last image to be transferred. The user exits the scanner software and enters the root directory of the scanner system. The user enters the file and reviews the filenames of the listed images. The user exits the file manager and transfers the images to a server by entering the following

| UNIX commands: |
| --- |
| cd dbase |
| cd matrix |
| ftp |
| open <server address> |
| <username> |
| <password> |
| cd ct_images |
| bin |
| prompt |
| mput <image filename> |

When the transfer is complete, the user enters "bye" and exits the root directory.

Once the images are stored on the server as described above, they may be imported into the AnalyzePC software on the computing device. To import the images into the software, the user copies all the image files relating to a particular article from the server and to a file folder on the computer hard drive. The user then opens the AnalyzePC software and selects the import/export module. The user selects the "volume tool" icon and then "describe raw data". The user sets "volume height" to 512 and "volume width" to 512. The "volume depth" is set to specify by "file list". The user sets "data type" to unsigned 16-bit and "byte offset" to 0 per file. The voxel height and width are not selected. The "byte swap" is set to pairs and "flip Y" is selected. In the "volume tool" menu, the user selects "wild cards". The user selects the files from the directory containing the image files they wish to import. The user then saves the imported files. The user exits the "import/export" module and enters the "load as" module. The user selects the file to be loaded and enters a heading to describe the file. The user selects "load" and then "save". The data from the article 44 is now ready for analysis.

Figure 9:
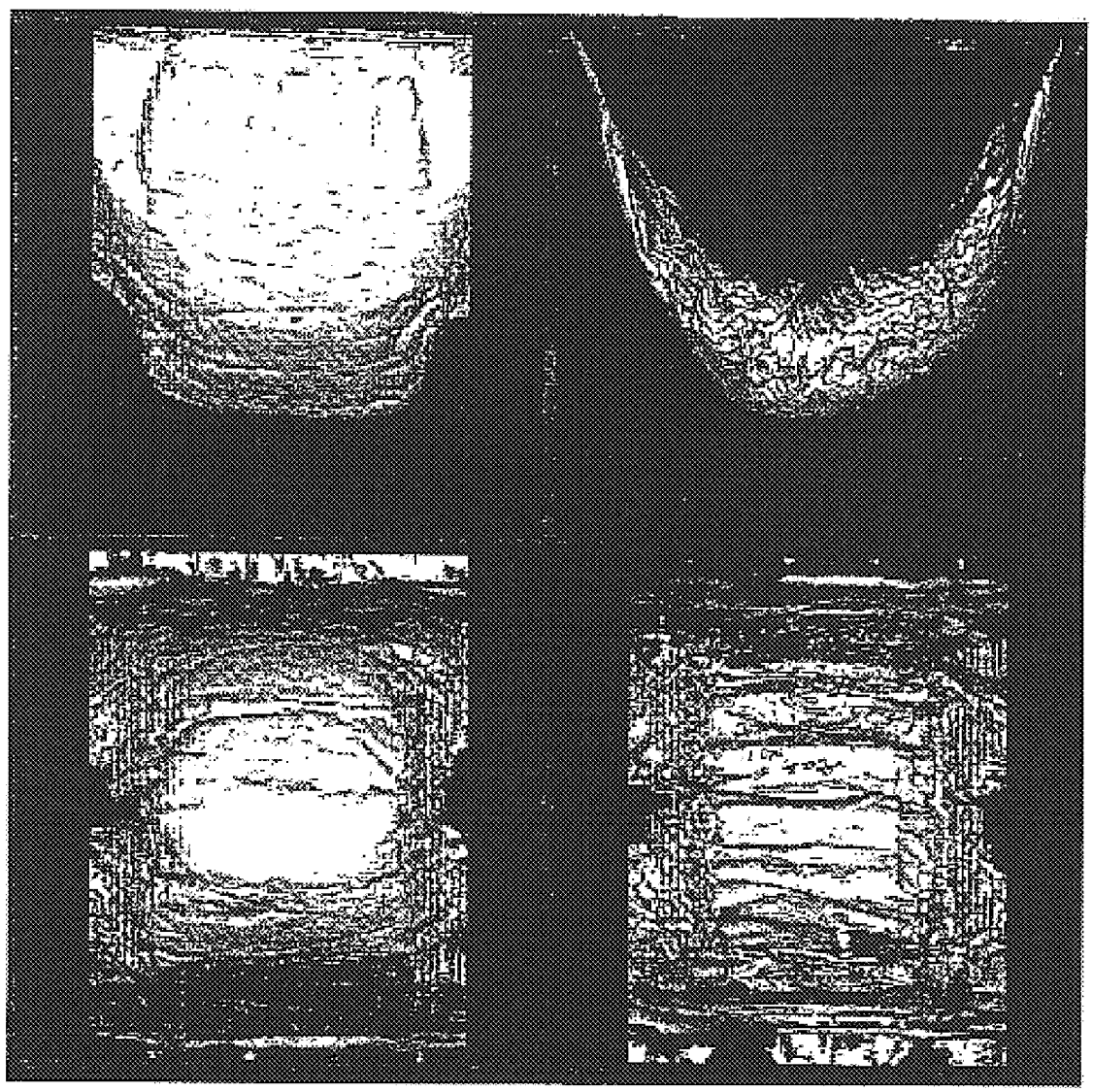
FIG. 9 is a computer display showing the article.

Once the image is loaded into the main menu, there are several analysis tools which can be used. For example, to view an article 44 in its 3D form, the user selects the "volume render" icon. By rendering the article image file in this window, the user can see that the conversion process from raw CT data to a readable image file is successful. To manipulate the 3D image, the user rotates it. The user can then display the article on the monitor 46 from any angle. An example of such a display is shown in FIG. 9.

Figure 10:
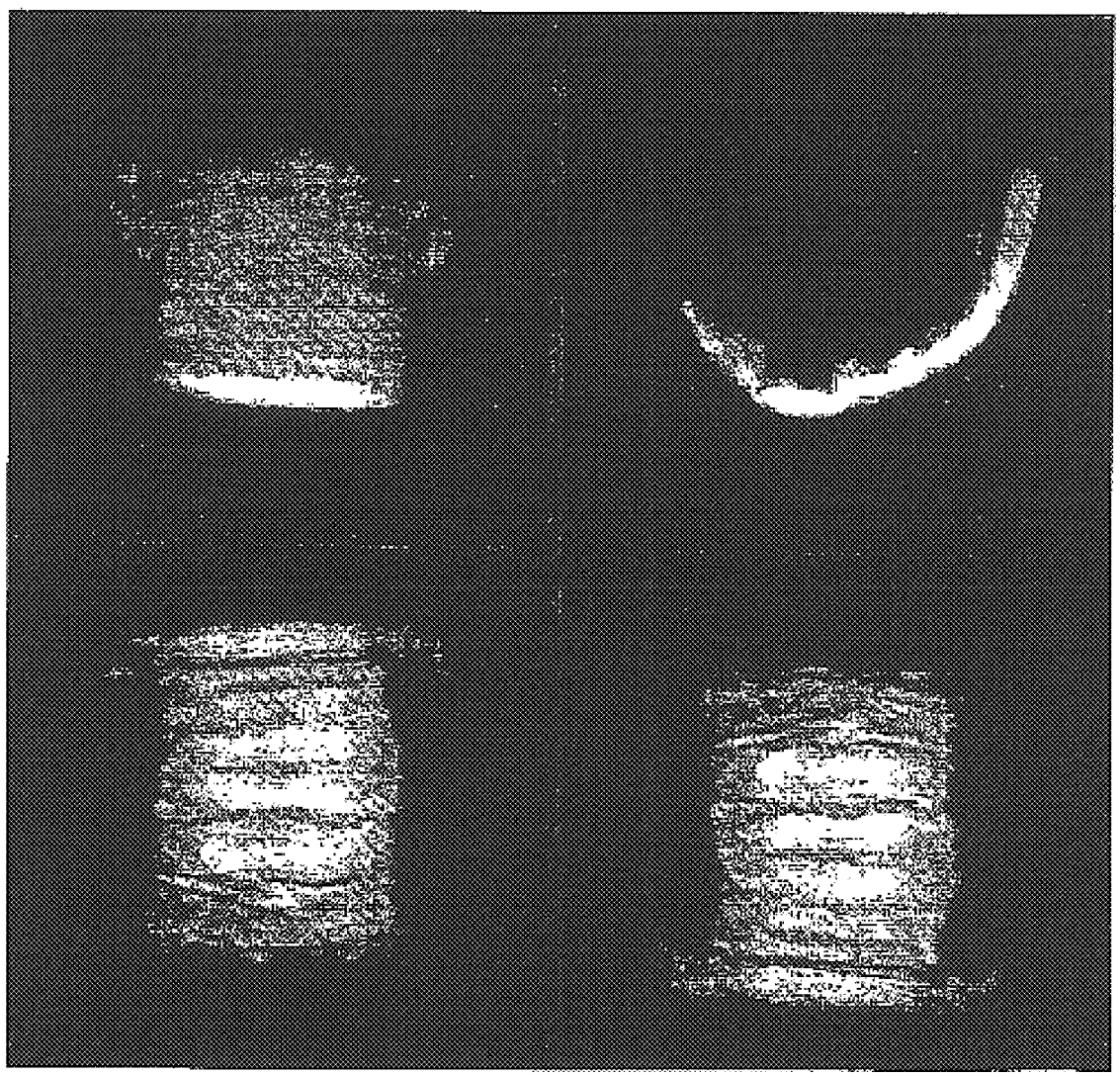
FIG. 10 is a computer display showing a visualization of liquid in the article.

The user can also display a visualization of the liquid within the article 44. An example of such a display is shown in FIG. 10. This display is created by summed voxel projection and shows a density gradient throughout the article. As in any x-ray, the higher the density, the whiter the area appears. In FIG. 10, the white portion shows where the liquid is located in the article 44. The gray area represents dry portions of the article 44 and the black area represents air.

The user can also display the liquid without the article 44. Since the liquid is bonded with the super absorbent of some articles and contained within the fluff of the article, it is not possible in those articles to separate the liquid from the article. When the liquid is analytically extracted, the super absorbent and fluff will also be extracted due to the density change within the article 44. Fluff, which typically is low in density, takes on the density of water when the water is contained within the fluff. In order to extract the liquid filled portion of the article using AnalyzePC, the user selects the "object extractor" icon. Once in the object extractor mode, the user selects the "define region" icon. An image of the article 44 will appear in a separate window. The user selects the orientation they wish to use to extract (e.g., a sagittal view). It may be desirable to select an orientation in which the entire absorbent core is visible to make the extraction process complete. If the user is unable to view the entire portion they wish to extract, part of the article may be missed during the extraction process.

Figure 12:
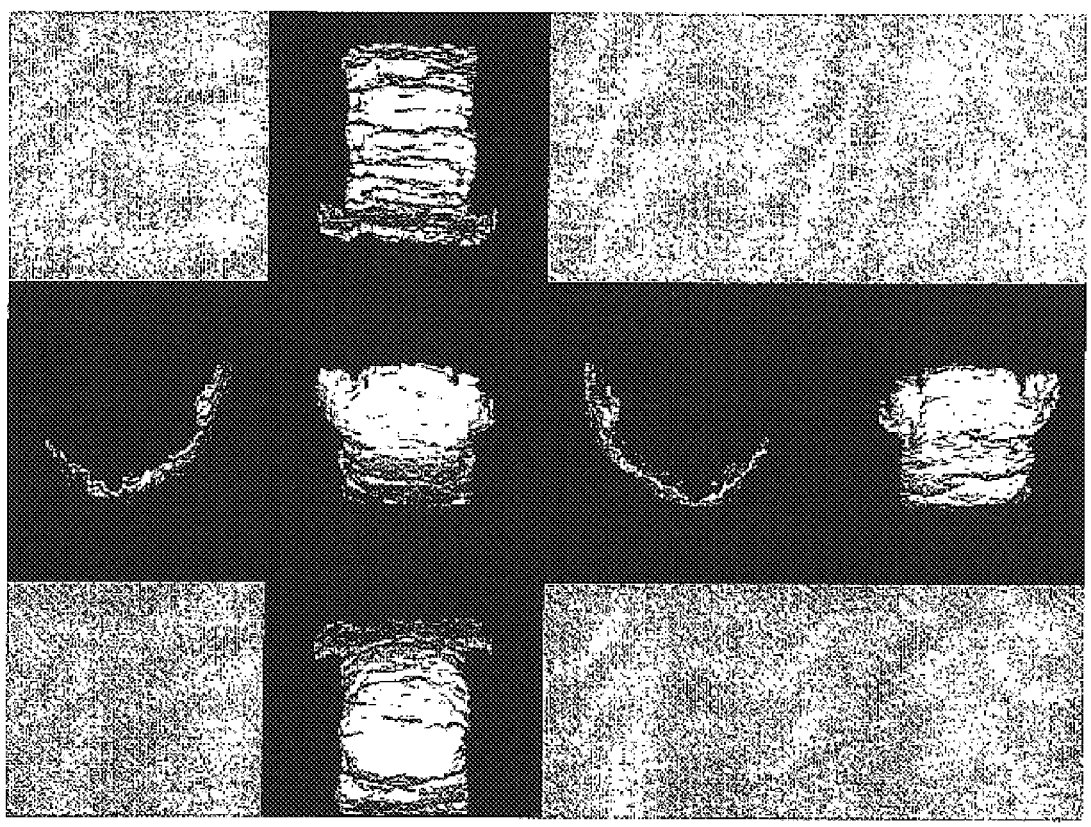
FIG. 12 is a computer display showing the article after extraction.
Figure 13:
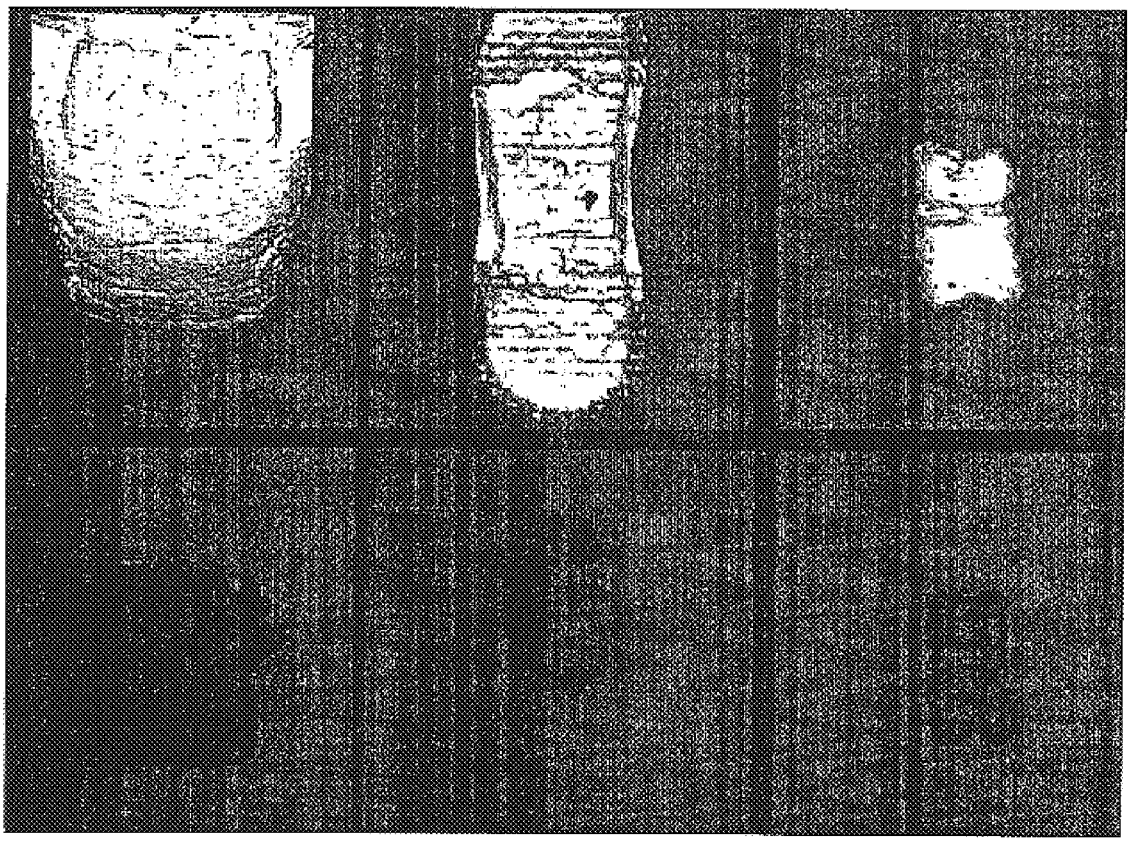
FIG. 13 is a computer display showing three different articles and extracted views thereof.
Figure 14:
FIG. 14 is a computer display showing view of an article having an overlaid extracted view.

To start extraction, the user sets a seed point. This is done by placing the arrow curser anywhere within the portion to be extracted. This will begin a seed growing process. A threshold max/min bar will appear. It is desirable to keep the "auto tract" selected. The user slides the ends of the threshold bar until they have encompassed the entire portion they want extracted. To the right of the original article image will appear the portion selected for extraction. The user will see an outline forming on the original image. An example of this display is shown in FIG. 11. Once the region is selected, the user selects the "extract object" icon. The extraction process will take place. The extracted object will now be displayed in all positions, front, back, left, right, top and bottom. By extracting an object, an object map is created and can be saved if desired. By saving an object map, the user can use it later for different applications and manipulations. FIG. 12 shows the display after extraction. FIG. 13 illustrates three different articles and extracted views similar to that described above. FIG. 14 illustrates an article having an overlaid extracted view showing the position of the liquid in the article.

As a specific example, a Step 2 Huggies Supreme disposable diaper was used as a test article. The diaper was insulted with 0.9% saline. (Huggies is a federally registered trademark of Kimberly-Clark Corporation of Neenah, Wis.) The diaper was weighed before and after the insult to determine 116.88 ml of saline was in the diaper. The diaper was CT scanned using 120 KV, 20 MA, a 250 FOV and slice thickness of 5 mm. Thirty-one sagittal slices were obtained. Once the object map of the article was created as described above, the "region of interest" window was opened to calculate statistical data related to the article. In the "region of interest" window, the maximum/minimum parameters were selected. The maximum parameter equals the largest density pixel which will be extracted and the minimum parameter equals the lowest density pixel which will be extracted. The maximum parameter is set to the maximum density available. Trial and error was used to determine the minimum parameter. The minimum parameter corresponds to saline within fluff and can be used for all subsequent analyses of similar articles formed from components made with the same manufacturing processes. Since the amount of saline in the diaper was known, the minimum number was selected by trial and error until the calculated volume approximately equaled the known volume. For the particular trial diaper, the maximum limit was 1211. To sum these data points, summing was turned on. Since each data point represented a cubic millimeter, the sum of the data points divided by 1000 equaled milliliters. The minimum threshold was adjusted until the sum of the data points divided by 1000 equaled the volume of the saline (i.e., 116.88 ml). After several iterations, a minimum threshold of 560 provided a result of 116.783 ml. FIG. 15 illustrates the software display at this point in the analysis.

Once the limits were set, the results were logged. First, the summing was turned off so that each slice would be logged. After each slice was logged, the summing was turned on to log the sum of all the slice data. The results of this log are shown in FIG. 16.

A subsequent test was performed to verify repeatability. Five Step 3 Huggies Supreme diapers having similar components were each scanned four times using different scanning techniques. The four scanning techniques were: 3 mm slice thickness with a 250 FOV; 5 mm slice thickness with a 250 FOV; 3 mm slice thickness with a 225 FOV; and 5 mm slice thickness with a 225 FOV. Each diaper was insulted with approximately 200 ml of 0.9% saline and allowed to stand for 20 minutes to allow wicking and to allow the suberabsorbent material in the diaper to expand. Each diaper was weighed before and after scanning and the difference calculated for verification of the analysis process. Since each diaper was scanned four times, there was a potential for some of the liquid to evaporate over the period of time it took to scan. It was determined that up to about 5 ml of liquid would evaporate from the time it was initially loaded to the time just after the fourth scan. The time lapse was about 30 to about 45 minutes from the start of the first sequence to the end of the last sequence. When scanning was complete, each of the twenty sequences were imported, converted and loaded into the AnalyzePC software. Each article was analyzed for liquid volume using the "Region of Interest" option. The threshold was set for all 20 files based on the first sequence analyzed. The first sequences threshold levels were 600 to 1125. The results were as follows:

| FILE NUMBER | CALCULATED VOLUME (ml) | MEASURED VOLUME (ml) |
|---|---|---|
| 1 | 200.42 | 200.24 |
| 2 | 199.50 | 199.42 |
| 3 | 199.52 | 198.60 |
| 4 | 198.72 | 197.78 |
| 5 | 201.02 | 200.18 |
| 6 | 199.29 | 198.75 |
| 7 | 199.45 | 197.32 |
| 8 | 196.61 | 197.32 |
| 9 | 203.97 | 202.61 |
| 10 | 202.42 | 200.76 |
| 11 | 202.20 | 198.91 |
| 12 | 200.88 | 197.04 |
| 13 | 205.58 | 202.02 |
| 14 | 203.26 | 201.19 |
| 15 | 204.98 | 200.36 |
| 16 | 203.01 | 199.54 |
| 17 | 206.11 | 201.86 |
| 18 | 204.63 | 200.99 |
| 19 | 206.00 | 200.12 |
| 20 | 204.51 | 199.26 |

The 95% confidence level for these results was 202.1 ml ±1.29 ml.

As another example, a tampon was scanned and analyzed with the AnalyzePC software. The tampon was weighed, insulted with 7.96 ml of 0.9% saline, allowed to sit for 20 minutes and weighed again before scanning. The tampon was scanned with a 2 mm slice thickness and a FOV of 125. Scan was performed sagittally. The image file was imported, converted and loaded. Through a trial and error process, it was determined that the threshold limits for the tampon were 315 and 1119, giving a calculated liquid volume of 7.962 ml.

As yet another example, a feminine pad was scanned and analyzed with the AnalyzePC software. The pad was weighed, insulted with 19.11 ml of 0.9% saline, allowed to sit for 20 min and weighed again before scanning. The pad was scanned with a slice thickness of 5 mm and a FOV of 125. The scanning was done coronally. The image file was imported, converted and loaded. The threshold limits for the pad were found to be 425 and 1101, giving a liquid volume of 18.82 ml.

Subsequent to the pad test described above, ten Kotex Ultrathin Maxi with wings feminine pads were scanned using two different scanning techniques to determine the repeatability of the measurements. (Kotex is a federally registered trademark of Kimberly-Clark Corporation of Neenah Wis.) One scanning technique used a 3 mm slice thickness at a 250 FOV and the other used a 5 mm slice thickness at a 250 FOV. The pad was scanned sagittally. Each pad was weighed, insulted with 5.5 ml of 0.9% saline, allowed to sit for 5 minutes, scanned and weighed again. Each image file was analyzed as described above and the threshold limit was found to be 550 to 1125. The results were as follows:

| FILE NUMBER | CALCULATED VOLUME (ml) | MEASURED VOLUME (ml) |
|---|---|---|
| 1 | 5.582 | 5.59 |
| 2 | 5.426 | 5.47 |
| 3 | 5.933 | 5.66 |
| 4 | 5.777 | 5.52 |
| 5 | 5.604 | 5.49 |
| 6 | 5.448 | 5.37 |
| 7 | 5.534 | 5.39 |
| 8 | 5.428 | 5.25 |
| 9 | 5.529 | 5.68 |
| 10 | 5.340 | 5.61 |
| 11 | 5.616 | 5.61 |
| 12 | 5.629 | 5.61 |
| 13 | 5.573 | 5.47 |
| 14 | 5.292 | 5.36 |
| 15 | 5.333 | 5.59 |
| 16 | 5.095 | 5.48 |
| 17 | 5.549 | 5.55 |
| 18 | 5.467 | 5.38 |
| 19 | 5.275 | 5.60 |
| 20 | 5.115 | 5.47 |

The 95% confidence level for these results was 5.477 ml ±0.079 ml.

As will be appreciated by those skilled in the art, the previously described system and process may be used to analyze liquid distribution and location, article deformation, liquid volume, absorbent core integrity, absorbent interlayer adhesive integrity, containment flap efficacy, Super Absorbent Material (SAM) location, absorbent core bulk or swell and article fit. Further, various system capabilities can be employed including non-destructive slice dissection, two-dimensional density imaging, three-dimensional surface rendering, and cross-sectional imaging.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A radiological system for analyzing an absorbent article comprising:
   a radiological device for collecting radiological data from the absorbent article;
   a support comprising a generally radiolucent frame having a central opening and at least one independent filament extending across the opening for holding the absorbent article in a position for the radiological device to collect data therefrom; and
   a computing device operatively connected to the radiological device having a program for analyzing the data collected by the radiological device.

2. A radiological system as set forth in claim 1 wherein the radiological device comprises a computed tomography scanner.

3. A radiological system as set forth in claim 1 further comprising an absorbent article from which radiological data is collected.

4. A radiological system as set forth in claim 3 wherein the programmed computing device is programmed to locate regions of the absorbent article containing liquid and those containing no liquid.

5. A radiological system as set forth in claim 4 wherein the programmed computing device is programmed to calculate the volume of the liquid contained in the absorbent article.

6. A radiological system as set forth in claim 3 wherein the programmed computing device is programmed to analyze the integrity of the absorbent article.

7. A radiological system as set forth in claim 3 wherein the programmed computing device is programmed to analyze deformation of the absorbent article.

8. A radiological system as set forth in claim 3 wherein the absorbent article includes a super absorbent material, and wherein the programmed computing device is programmed to determine the location of a super absorbent material.

9. In combination,
an absorbent personal care article,
a liquid absorbed by the absorbent personal care article and distributed within the absorbent article,
a support for holding the absorbent article,
a computed tomography scanner located adjacent the support for collecting radiological data from the absorbent personal care article held by the support, and
a programmed computing device for analyzing the collected data electronically transferred to the programming device from the computed tomography scanner to determine a volume of liquid absorbed by and distributed within the absorbent personal care article.

10. The combination as set forth in claim 9 wherein the personal care article is selected from a group including feminine care articles, diapers, training pants, child and infant care articles, incontinence articles, and adult care articles used to absorb body waste.

11. The combination as set forth in claim 10 wherein the programmed computing device determines the volume of the liquid absorbed by the absorbent personal care article within about a 95 percent confidence level.

12. The combination as set forth in claim 9 wherein the liquid comprises a synthetic body waste.

13. The combination as set forth in claim 12 wherein the synthetic body waste is a synthetic urine.

14. The combination as set forth in claim 9 wherein the programmed computing device is programmed to analyze deformation of the absorbent article.

15. The combination as set forth in claim 9 wherein the absorbent article comprises an absorbent core and the programmed computing device is programmed to analyze the integrity of the absorbent core.

16. The combination as set forth in claim 9 wherein the absorbent personal care article includes a super absorbent material, and wherein the programmed computing device is programmed to determine the location of a super absorbent material.

17. A method of nondestructively determining a volume of a liquid distributed within an absorbent personal card article comprising:
positioning an absorbent personal care article containing a liquid on a support;
aligning the support supporting the absorbent article with a computed tomography scanner;
collecting radiological data from the absorbent article using the computed tomography scanner;
electronically transferring the collected data to a programmed computing device; and
analyzing the collected data using the programmed computing device to determine the volume of liquid distributed within the absorbent personal care article.

18. A method as set forth in claim 17 wherein the step of collecting radiological data from the article includes:
scanning the article at a plurality of data points, each of said plurality of data points corresponding to a portion of the absorbent article having a predetermined volume; and
determining a relative density of each of said plurality of data points.

19. A method as set forth in claim 18 further comprising;
establishing a maximum threshold limit and a minimum threshold limit;
summing the predetermined volumes of every data point of said plurality of data points having a relative density greater than the minimum threshold and less than the maximum threshold;
wherein the sum of the predetermined volumes is approximately the volume of the liquid contained in the absorbent article.

20. A method as set forth in claim 19 wherein summing the predetermined volumes determines the volume of the liquid contained in the absorbent personal care article within about a 95 percent confidence level.

21. A method as set forth in claim 17 wherein the absorbent article further comprises an absorbent core, and wherein said step of analyzing the collected data using the programmed computing device further comprises locating and calculating the volumes of liquid distributed throughout the absorbent core.

22. A method as set forth in claim 17 wherein the step of positioning the absorbent personal care article comprising positioning an article selected from a group including feminine care articles, diapers, training pants, child and infant care articles, incontinence articles, and adult care articles used to absorb body waste.

23. A method as set forth in claim 17 further comprising wetting the absorbent personal care article with a synthetic body waste.

24. A method as set forth in claim 23 wherein the synthetic body waste is a synthetic urine.

25. A method as set forth in claim 17 wherein the step of analyzing the collected data using the programmed computing device further comprises analyzing deformation of the absorbent article.

26. A method as set forth in claim 17 wherein the step of analyzing the collected data using the programmed computing device further comprises analyzing the integrity of an absorbent core of the absorbent article.

27. A method as Set forth in claim 17 wherein the absorbent personal care article includes a super absorbent material, and wherein the step of analyzing the collected data using the programmed computing device further comprises determining the location of a super absorbent material.

28. In combination,
an absorbent personal care article,
a liquid absorbed by the absorbent personal care article and distributed within the absorbent article,
a support for holding the absorbent article,
a computed tomography scanner mounted adjacent the support for collecting radiological data from the absorbent personal care article held by the support, and
a programmed computing device for analyzing the collected data electronically transferred to the programming device from the computed tomography scanner to determine a three-dimensional distribution of liquid absorbed by the absorbent personal care article.

29. The combination as set forth in claim 28 wherein the personal care article is selected from a group including feminine care articles, diapers, training pants, child and infant care articles, incontinence articles, and adult care articles used to absorb body waste.

30. The combination as set forth in claim 28 wherein the liquid comprises a synthetic body waste.

31. The combination as set forth in claim 30 wherein the synthetic body waste is a synthetic urine.

32. A method of nondestructively determining liquid distribution within an absorbent personal care article comprising:
   positioning an absorbent personal care article containing a liquid on a support;
   aligning the support supporting the absorbent article with a computed tomography scanner;
   collecting radiological data from the absorbent article using the computed tomography scanner;
   electronically transferring the collected data to a programmed computing device; and
   analyzing the collected data using the programmed computing device to determine a three-dimensional distribution of liquid within the absorbent personal care article.

33. A method as set forth in claim 32 wherein the absorbent article further comprises an absorbent core, and wherein said step of analyzing the collected data using the programmed computing device further comprises determining the three-dimensional distribution of liquid throughout the absorbent core.

34. A method as set forth in claim 32 wherein the step of positioning the absorbent personal care article comprising positioning an article selected from a group including feminine care articles, diapers, training pants, child and infant care articles, incontinence articles, and adult care articles used to absorb body waste.

35. A method as set forth in claim 32 further comprising wetting the absorbent personal care article with a synthetic body waste.

36. A method as set forth in claim 35 wherein the synthetic body waste is a synthetic urine.

* * * * *